United States Patent [19]
Sorensen

[11] Patent Number: 6,074,815
[45] Date of Patent: Jun. 13, 2000

[54] SELECTION OF TEST SPECIES FOR TESTING TO IDENTIFY COMPONENTS THEREOF THAT DELETERIOUSLY AFFECT A TARGET SPECIES MEMBER

[75] Inventor: Jens Ole Sorensen, Grand Cayman, Cayman Islands

[73] Assignee: Universal Ventures, Cayman Islands

[21] Appl. No.: 09/264,118

[22] Filed: Mar. 8, 1999

[51] Int. Cl.[7] .............................. C12Q 1/00; C12Q 1/02; C12Q 33/567; C12Q 33/53

[52] U.S. Cl. ................................ 435/4; 435/29; 435/7.21; 435/7.22; 435/7.23; 435/253.1; 435/253.3; 426/665; 426/231

[58] Field of Search ................................ 435/4, 29, 7.21, 435/7.22, 7.23, 253.1, 253.3; 426/665, 231

[56] References Cited

U.S. PATENT DOCUMENTS

| | | | |
|---|---|---|---|
| 4,878,891 | 11/1989 | Judy et al. | 435/4 |
| 5,439,924 | 8/1995 | Miller | 435/4 |
| 5,527,700 | 6/1996 | Kaslow et al. | 435/4 |
| 5,843,698 | 12/1998 | Sorensen | 435/4 |

OTHER PUBLICATIONS

Blakely, "The Good Virus", Discover, Nov. 1996, pp. 50 et seq.

Hall, "Eat To Fight Cancer", Health, Apr. 1997, pp. 108 et esq.

Primary Examiner—Louise N. Leary

Attorney, Agent, or Firm—Edward W. Callan

[57] ABSTRACT

A component of a member of a test species that deleteriously affects a target species that is a parasite of an adjoiner species is identified by a method including the steps of (a) selecting the test species from among test species that are attached or internal to a member of the adjoiner species whom was exposed to the target species but did not react adversely thereto as did other exposed members of the adjoiner species; (b) separating at least one member of the selected test species into a plurality of components; (c) exposing at least some of the separated components of the member(s) of the test species separately to members of the target species; and (d) examining such exposures to determine for such identification whether members of the target species have been deleteriously affected by such exposures. The test species may be a symbiont or a traditional food source of the adjoiner species. A product including such a test-species component identified as deleteriously affecting members of a target species and/or an equivalent of the identified component is manufactured either by separating the identified component in bulk quantities from members of the test species or by synthesizing the identified component and/or an equivalent of the identified component in bulk quantities. The product is tested to determine the extent of any deleterious effect upon the adjoiner species and the extent of the deleterious effect of the product upon the target species. The method of manufacturing the product may further include modifying the product to decrease any deleterious effect upon the adjoiner species and/or modifying the product to increase the deleterious effect upon the target species.

29 Claims, 3 Drawing Sheets

```
┌─────────────────────────────────────────────────────────────────┐
│ SELECT MEMBER OF TEST SPECIES FROM AMONG SPECIES ATTACHED OR    │
│ INTERNAL TO ADJOINER SPECIES MEMBER WHOM WAS EXPOSED TO         │
│ TARGET SPECIES AND REACTED ADVERSELY THERETO BUT THEN           │
│ RECOVERED                                                       │
│   ┌─────────────────────────────────────────────────────────┐   │
│   │ SYMBIONT OF AN ADJOINER SPECIES TO THE TARGET SPECIES   │   │
│   └─────────────────────────────────────────────────────────┘   │
│   ┌─────────────────────────────────────────────────────────┐   │
│   │ TRADITIONAL FOOD SOURCE OF THE ADJOINER SPECIES         │   │
│   └─────────────────────────────────────────────────────────┘   │
└─────────────────────────────────────────────────────────────────┘
                              │                           ╲30
                              ▼
      ┌──────────────────────────────────────────────────┐
      │ SEPARATE SELECTED TEST-SPECIES MEMBER INTO COMPONENTS │
      └──────────────────────────────────────────────────┘
                              │                 ╲32
                              ▼
      ┌──────────────────────────────────────────┐
      │ EXPOSE SEPARATED TEST-SPECIES COMPONENTS │─34
      │ TO THE TARGET SPECIES                    │
      └──────────────────────────────────────────┘
                              │
                              ▼
      ┌──────────────────────────────────────────────┐
      │ EXAMINE EXPOSURE TO DETERMINE WHETHER THE    │─36
      │ TARGET SPECIES HAS BEEN DELETERIOUSLY AFFECTED│
      └──────────────────────────────────────────────┘
```

FIG.3

```
          40                              42
           )                               )
  ┌────────────────────┐        ┌──────────────────────────┐
  │ SEPARATE IDENTIFIED│        │ SYNTHESIZE IDENTIFIED    │
  │ COMPONENT FROM     │        │ COMPONENT OR EQUIVALENT  │
  │ TEST SPECIES IN    │        │ OF IDENTIFIED COMPONENT  │
  │ BULK QUANTITIES    │        │ IN BULK QUANTITIES       │
  └────────────────────┘        └──────────────────────────┘
            │                              │
     44     │                              │     46
      )     │                              │      (
  ┌───▼──────────────────┐        ┌────────▼─────────────┐
  │ MODIFY TO DECREASE   │        │ MODIFY TO INCREASE   │
  │ DELETERIOUS EFFECT UPON│      │ DELETERIOUS EFFECT   │
  │ ADJOINER SPECIES     │        │ UPON TARGET SPECIES  │
  └──────────────────────┘        └──────────────────────┘
```

SELECTION OF TEST SPECIES FOR TESTING TO IDENTIFY COMPONENTS THEREOF THAT DELETERIOUSLY AFFECT A TARGET SPECIES MEMBER

BACKGROUND OF THE INVENTION

The present invention generally pertains to materials that deleteriously affect members of a target species and is particularly directed to selection of test species as well as to identifying, manufacturing, testing and using such materials.

It has been known to identify components of members of test species that deleteriously affect members of a target species by a method including the steps of:

(a) separating at least one member of each of a plurality of test species into a plurality of components;

(b) exposing at least some of said separated components of said member(s) of the test species separately to members of the target species; and (c) examining said exposures to determine for said identification whether members of the target species have been deleteriously affected by said exposures.

This method has been conducted to identify materials that are deleterious to a target species that is a symbiont of an adjoiner species, such as a parasite of the adjoiner species. Although such identification method has been practiced with test species that are symbionts or traditional food sources of the adjoiner species, it is believed that such symbiotic relationship and such food-source relationship between the test species and the adjoiner species have been merely incidental to broad screenings of a plurality of different test species based upon their chemical compositions rather than an intentional aspect of the method. A food source includes plants and animals and secretions and waste products therefrom, such as honey, pollen, sap, milk, feces and urine.

Symbiotic relationships between different species include (a) a parasitic relationship, wherein one species benefits from the relationship and the other species is harmed by the relationship; (b) mutualism, wherein both species benefit from the relationship; (c) commensalism, wherein one species benefits from the relationship and the other species is unaffected by the relationship; and (d) amensalism, wherein one species is harmed by the relationship and the other species is unaffected by the relationship.

SUMMARY OF THE INVENTION

The present invention provides a method of identifying components of members of test species that deleteriously affect members of a target species, comprising the steps of:

(a) separating at least one member of a test species into a plurality of components;

(b) exposing at least some of said separated components of said member(s) of the test species separately to members of the target species, wherein the target species is a symbiont of an adjoiner species;

(c) examining said exposures to determine for said identification whether members of the target species have been deleteriously affected by said exposures; and (d) selecting the test species from among test species that are attached or internal to a member of the adjoiner species whom has not reacted to the target species as adversely as other members of the adjoiner species.

The present invention provides each separated component of a member of a test species identified by any of the above-described identification methods as deleteriously affecting members of a target species or an equivalent of said identified component.

The present invention further provides methods of manufacturing products including a test-species component identified by any of the foregoing methods as deleteriously affecting members of a target species and/or an equivalent of said identified component, as described below in the detailed description of the preferred embodiments.

The present invention also provides products manufactured according to such methods of manufacture.

The present invention additionally provides methods of using and testing products manufactured according to such methods of manufacture, as described below in the detailed description of the preferred embodiments.

Additional features of the present invention are described with reference to the detailed description of the preferred embodiments.

BRIEF DESCRIPTION OF THE DRAWING

FIG. 3 is a block diagram of a further preferred embodiment of the identification method of the present invention.

FIG. 4 is a block diagram showing preferred embodiments of product manufacturing methods according to the present invention

DETAILED DESCRIPTION

In the various embodiments of the present invention described herein, the adjoiner species include but are not limited to the human species, a species having a near-human-species genetic composition, such as chimpanzees and pigs, and other species afflicted with parasitic diseases; the target species include but are not limited to HIV (the AIDS-causing virus), cancer causing viruses, *E.coli* bacteria, histoplasma capsulatum (which causes histoplasinosis), borrelia burgdoferi (which causes Lime's disease), the typhoid fever causing virus, the Norwalk virus and the rotovirus; and the test species include but are not limited to plasmodium falciparum, plasmodium ovale, plasmodium vivax, and plasmodium malariae (all four of which are species of malaria), treponema pallidum (syphilis), the smallpox virus, mycobacterium tuberculosis, ascaris lumbricoides (tapeworm), deratophyte (athlete's foot), helicobacter pylori (ulcer-causing bacteria) and traditional food sources of the adjoiner species, including co-evolutionary food sources of the adjoiner species that previously had not been known to be food sources of the adjoiner species.

Figure 1:
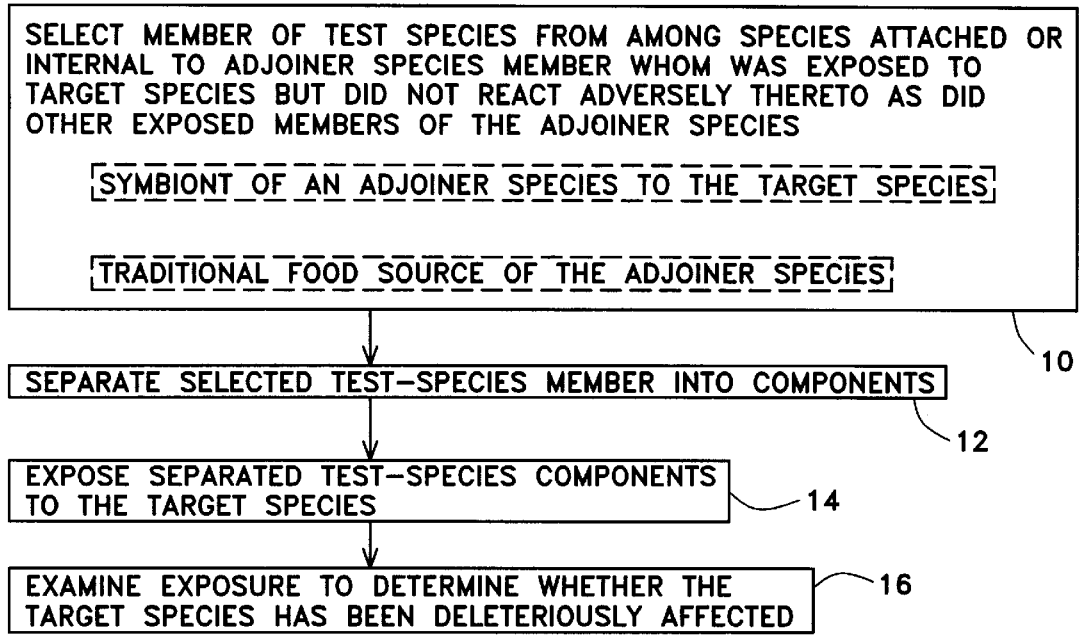
FIG. 1 is a block diagram of one preferred embodiment of the identification method of the present invention.

Referring to FIG. 1, one preferred embodiment of the method of the present invention of identifying components of members of test species that deleteriously affect members of a target species that is a symbiont of a given adjoiner species includes a step 10 of selecting a test species from among species that are attached to an adjoiner species member whom was exposed to the target species but did not react adversely thereto as did other exposed members of the adjoiner species; a step 12 of separating at least one member of the selected test species into a plurality of components; a step 14 of exposing at least some of the separated components of the member(s) of the test species separately to members of the target species; and a step 16 of examining such exposures to determine for such identification whether members of the target species have been deleteriously affected by such exposures.

Figure 2:
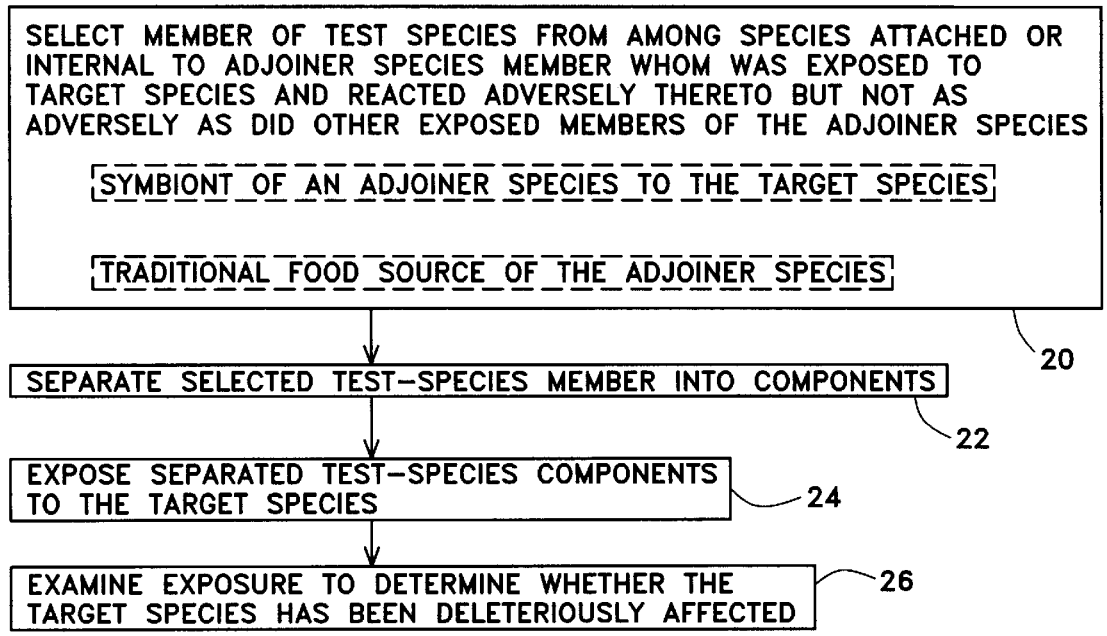
FIG. 2 is a block diagram of another preferred embodiment of the identification method of the present invention.

Referring to FIG. 2, another preferred embodiment of the method of the present invention of identifying components of members of test species that deleteriously affect members of a target species that is a symbiont of a given adjoiner species includes a step 20 of selecting a test species from among species that are attached to an adjoiner species member whom was exposed to the target species and reacted adversely thereto but not as adversely as did other exposed members of the adjoiner species; a step 22 of separating at least one member of the selected test species into a plurality of components; a step 24 of exposing at least some of the separated components of the member(s) of the test species separately to members of the target species; and a step 26 of examining such exposures to determine for such identification whether members of the target species have been deleteriously affected by such exposures.

Referring to FIG. 3, a further preferred embodiment of the method of the present invention of identifying components of members of test species that deleteriously affect members of a target species that is a symbiont of a given adjoiner species includes a step 30 of selecting a test species from among species that are attached to an adjoiner species member; a step 32 of separating at least one member of the selected test species into a plurality of components; a step 34 of exposing at least some of the separated components of the member(s) of the test species separately to members of the target species; and a step 36 of examining such exposures to determine for such identification whether members of the target species have been deleteriously affected by such exposures.

In some preferred embodiments, the test species are symbionts or traditional food sources of the adjoiner species.

In some preferred embodiments, the separation step 12, 22, 32 the exposure step 14, 24, 34 and the examination step 16, 26, 36 are executed methodically and systematically with a large number of test species that are symbionts of the adjoiner species.

In some preferred embodiments, the separation step 12, 22, 32 the exposure step 14, 24, 34 and the examination step 16, 26, 36 are executed methodically and systematically with a large number of test species that are traditional food sources of the adjoiner species.

In some preferred embodiments, the separation step 12, 22, 32 is executed with such a large number of test species that are symbionts of the adjoiner species that the ratio of execution of the separation step 12, 22, 32 when the test species are symbionts of the adjoiner species relative to execution of the separation step 12, 22, 32 when the test species are not symbionts of the adjoiner species is significantly higher than said ratio of execution according to the prior art.

In some preferred embodiments, the separation step 12, 22, 32 is executed with such a large number of test species that are traditional food sources of the adjoiner species that the ratio of execution of the separation step 12, 22, 32 when the test species are traditional food sources of the adjoiner species relative to execution of the separation step 12, 22, 32 when the test species are not traditional food sources of the adjoiner species is significantly higher than said ratio of execution according to the prior art.

In some preferred embodiments, the exposure step 14, 24, 34 and the examination step 16, 26, 36 are executed in such large numbers when the test species are symbionts of the adjoiner species that the ratio of execution of the exposure step 14, 24, 34 and the examination step 16, 26, 36 when the test species are symbionts of the adjoiner species relative to execution of the exposure step 14, 24, 34 and the examination step 16, 26, 36 when the test species are not symbionts of the adjoiner species is significantly higher than said ratio of execution according to the prior art.

In some preferred embodiments, the exposure step 14, 24, 34 and the examination step 16, 26, 36 are executed in such large numbers when the test species are traditional food sources of the adjoiner species that the ratio of execution of the exposure step 14, 24, 34 and the examination step 16, 26, 36 when the test species are traditional food sources of the adjoiner species relative to execution of the exposure step 14, 24, 34 and the examination step 16, 26, 36 when the test species are not traditional food sources of the adjoiner species is significantly higher than said ratio of execution according to the prior art.

In some preferred embodiments of the methods described above, prior to the separation step 12, 22, 32, the method includes a step (not shown) of exposing at least a component of the target species to at least one member of the selected test species for the purpose of establishing any immunity of such target-species component to the selected test species as may be established.

In some embodiments of the above-described methods, members of the test species at least in some aspect deleteriously affect members of the adjoiner species.

In some embodiments of the above-described methods, members of the target species at least in some aspect deleteriously affect members of the adjoiner species.

Preferred embodiments of methods according to the present invention of manufacturing a product including a test-species component identified by any of the above-described methods as deleteriously affecting members of a target species and/or an equivalent of said identified component are described with reference to FIG. 4. The product is manufactured either by a step 40 of separating the identified component in bulk quantities from said members of said test species or by a step 42 of synthesizing the identified component and/or an equivalent of the identified component in bulk quantities. The manufacturing method may further include a step 44 of modifying the product to decrease any deleterious effect upon the adjoiner species caused by the identified component and/or the equivalent of the identified component; and/or a step 46 of modifying the product to increase the deleterious effect upon the target species caused by the identified component and/or the equivalent of the identified component. The deleterious effect can be modified by varying the quantity of the identified component and/or the equivalent of the identified component within the product.

Figure 5:
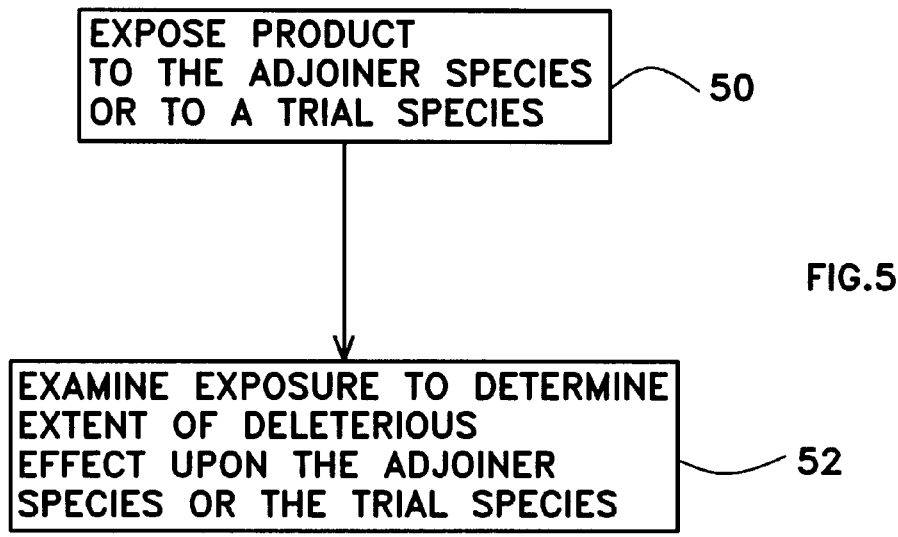
FIG. 5 is a block diagram of one preferred embodiment of a product testing method according to the present invention

Referring to FIG. 5, one preferred embodiment of a method according to the present invention of testing the above-described manufactured product, includes a step 50 of exposing the product to the adjoiner species or a member of a trial species; and a step 52 of examining such exposure to determine the extent of any deleterious effect upon the adjoiner species or the trial species respectively. Preferably, the trial species reacts to such exposure in a manner equivalent to such a reaction by the adjoiner species.

Figure 6:
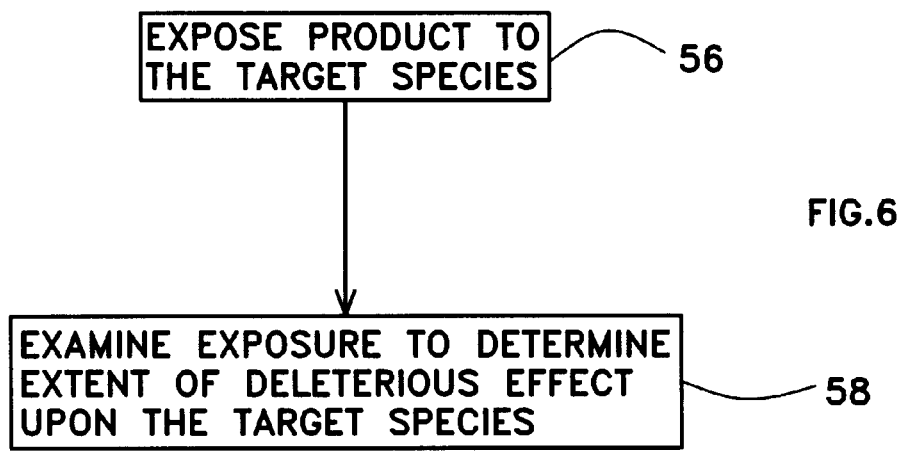
FIG. 6 is a block diagram of another preferred embodiment of a product testing method according to the present invention.

Referring to FIG. 6, another preferred embodiment of a method according to the present invention of testing the above-described manufactured product, includes a step 56 of exposing the product to the target species; and a step 58 of examining such exposure to determine the extent of the deleterious effect upon the target species.

A preferred embodiment (not shown) of a method according to the present invention of using a component of a member of a test species identified by any of the above-described methods and/or an equivalent of the identified component to treat an adjoiner species that is afflicted with a target species includes the step of exposing the identified component and/or the equivalent of the identified component to members of the target species that are residing in or on a member of the adjoiner species. Preferably, such exposure is accomplished by using a product manufactured by one of the above-described manufacturing methods.

In some, but not all, of the various embodiments of the deleterious-component identifying methods according to the present, it is preferred that during the step of exposing separated components of member(s) of the test species to members of the target species, the exposed members of the target species are isolated from the adjoiner species.

The advantages specifically stated herein do not necessarily apply to every conceivable embodiment of the present invention. Further, such stated advantages of the present invention are only examples and should not be construed as the only advantages of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

I claim:

1. A method of identifying components of members of test species that deleteriously affect members of a target species, comprising the steps of:
    (a) separating at least one member of a test species into a plurality of components;
    (b) exposing at least some of said separated components of said member(s) of the test species separately to members of the target species, wherein the target species is a symbiont of an adjoiner species;
    (c) examining said exposures to determine for said identification whether members of the target species have been deleteriously affected by said exposures; and
    (d) selecting the test species from among test species that are attached or internal to a member of the adjoiner species whom has not reacted to the target species as adversely as other members of the adjoiner species.

2. A method of identifying components of members of test species that deleteriously affect members of a target species, comprising the steps of:
    (a) separating at least one member of a test species into a plurality of components;
    (b) exposing at least some of said separated components of said member(s) of the test species separately to members of the target species, wherein the target species is a symbiont of an adjoiner species;
    (c) examining said exposures to determine for said identification whether members of the target species have been deleteriously affected by said exposures; and
    (d) selecting the test species from among test species that are attached or internal to a member of the adjoiner species whom was exposed to the target species but did not react adversely thereto as did other exposed members of the adjoiner species.

3. A method of identifying components of members of test species that deleteriously affect members of a target species, comprising the steps of:
    (a) separating at least one member of a test species into a plurality of components;
    (b) exposing at least some of said separated components of said member(s) of the test species separately to members of the target species, wherein the target species is a symbiont of an adjoiner species;
    (c) examining said exposures to determine for said identification whether members of the target species have been deleteriously affected by said exposures; and
    (d) selecting the test species from among test species that are attached or internal to a member of the adjoiner species whom was exposed to the target species and reacted adversely thereto but not as adversely as did other exposed members of the adjoiner species.

4. A method of identifying components of members of test species that deleteriously affect members of a target species, comprising the steps of:
    (a) separating at least one member of a test species into a plurality of components;
    (b) exposing at least some of said separated components of said member(s) of the test species separately to members of the target species, wherein the target species is a symbiont of an adjoiner species;
    (c) examining said exposures to determine for said identification whether members of the target species have been deleteriously affected by said exposures; and
    (d) selecting the test species from among test species that are attached or internal to a member of the adjoiner species whom was exposed to the target species and reacted adversely thereto but then recovered.

5. A method according to claim 1, 2, 3 or 4, wherein steps (a), (b) and (c) are executed methodically and systematically with a large number of test species that are symbionts of the adjoiner species.

6. A method according to claim 1, 2, 3 or 4, wherein step (a) is executed with such a large number of test species that are symbionts of the adjoiner species that the ratio of execution of step (a) when the test species are symbionts of the adjoiner species relative to execution of step (a) when the test species are not symbionts of the adjoiner species is significantly higher than said ratio of execution according to the prior art.

7. A method according to claim 1, 2, 3 or 4, wherein steps (b) and (c) are executed in such large numbers when the test species are symbionts of the adjoiner species that the ratio of execution of steps (b) and (c) when the test species are symbionts of the adjoiner species relative to execution of steps (b) and (c) when the test species are not symbionts of the adjoiner species is significantly higher than said ratio of execution according to the prior art.

8. A method according to claim 1, 2, 3 or 4, wherein steps (a), (b) and (c) are executed methodically and systematically with a large number of test species that are traditional food sources of the adjoiner species.

9. A method according to claim 1, 2, 3 or 4, wherein step (a) is executed with such a large number of test species that are traditional food sources of the adjoiner species that the ratio of execution of step (a) when the test species are traditional food sources of the adjoiner species relative to execution of step (a) when the test species are not traditional food sources of the adjoiner species is significantly higher than said ratio of execution according to the prior art.

10. A method according to claim 1, 2, 3 or 4, wherein steps (b) and (c) are executed in such large numbers when the test species are traditional food sources of the adjoiner species that the ratio of execution of steps (b) and (c) when the test species are traditional food sources of the adjoiner species relative to execution of steps (b) and (c) when the test species are not traditional food sources of the adjoiner species is significantly higher than said ratio of execution according to the prior art.

11. A method according to any of claims 1, 2, 3 or 4, wherein the adjoiner species is the human species.

12. A method according to any of claims 1, 2, 3 or 4, wherein the adjoiner species has a near-human-species genetic composition.

13. A separated component of a member of a test species identified by the method of any of claims 1, 2, 3 or 4 as deleteriously affecting members of a target species or an equivalent of said identified component.

14. A method of using a component of a member of a test species identified by the method of any of claims 1, 2, 3 or 4 as deleteriously affecting members of a target species and/or an equivalent of said identified component, comprising the step of:

(e) exposing said identified component and/or an equivalent of said identified component to members of the target species that are residing in or on a member of the adjoiner species.

15. A method of manufacturing a product including a test-species component identified by the method of any of claims 1, 2, 3 or 4 as deleteriously affecting members of a target species and/or an equivalent of said identified component, comprising the step of:

(e) providing said component in bulk quantities.

16. A product manufactured according to the method of claim 15.

17. A method according to claim 15, further comprising the step of:

(f) modifying the product to decrease any deleterious effect upon the adjoiner species caused by the identified component and/or said equivalent thereof.

18. A product manufactured according to the method of claim 17.

19. A method according to claim 15, further comprising the step of:

(f) modifying the product to increase the deleterious effect upon the target species caused by the identified component and/or said equivalent thereof.

20. A product manufactured according to the method of claim 19.

21. A method according to claim 15, wherein step (e) comprises separating said component in bulk quantities from said members of said test species.

22. A product manufactured according to the method of claim 21.

23. A method according to claim 15, wherein step (e) comprises synthesizing said component and/or an equivalent thereof in bulk quantities.

24. A product manufactured according to the method of claim 23.

25. A method of testing a product manufactured according to claim 15, comprising the steps of:

(f) exposing said product to the adjoiner species or a member of a trial species; and (g) examining said exposure of step (f) to determine the extent of any deleterious effect upon the adjoiner species or the trial species respectively.

26. A method of testing a product manufactured according to claim 15, comprising the steps of:

(f) exposing said product to the target species; and (g) examining said exposure of step (f) to determine the extent of the deleterious effect upon the target species.

27. A method according to claims 1, 2, 3 or 4, wherein members of the test species at least in some aspect deleteriously affect members of the adjoiner species.

28. A method according to claims 1, 2, 3 or 4, wherein members of the target species at least in some aspect deleteriously affect members of the adjoiner species.

29. A method according to claims 1, 2, 3 or 4, wherein during said step of exposing separated components of member(s) of said test species to members of the target species, said exposed members of the target species are isolated from the adjoiner species.

* * * * *

(12) EX PARTE REEXAMINATION CERTIFICATE (9652nd)
United States Patent
Sorensen

(10) Number: US 6,074,815 C1
(45) Certificate Issued: May 15, 2013

(54) SELECTION OF TEST SPECIES FOR TESTING TO IDENTIFY COMPONENTS THEREOF THAT DELETERIOUSLY AFFECT A TARGET SPECIES MEMBER

(75) Inventor: Jens Ole Sorensen, Grand Cayman (KY)

(73) Assignee: Sorensen Research and Development, San Diego, CA (US)

Reexamination Request:
No. 90/011,653, May 4, 2011

Reexamination Certificate for:
Patent No.: 6,074,815
Issued: Jun. 13, 2000
Appl. No.: 09/264,118
Filed: Mar. 8, 1999

(51) Int. Cl.
*G01N 35/50* (2006.01)

(52) U.S. Cl.
USPC ............. 435/4; 435/7.22; 435/29; 435/253.1; 435/253.3; 435/7.23; 426/231; 426/665

(58) Field of Classification Search
USPC ............................................................ 435/4
See application file for complete search history.

(56) References Cited

To view the complete listing of prior art documents cited during the proceeding for Reexamination Control Number 90/011,653, please refer to the USPTO's public Patent Application Information Retrieval (PAIR) system under the Display References tab.

*Primary Examiner* — Bruce Campbell

(57) ABSTRACT

A component of a member of a test species that deleteriously affects a target species that is a parasite of an adjoiner species is identified by a method including the steps of (a) selecting the test species from among test species that are attached or internal to a member of the adjoiner species whom was exposed to the target species but did not react adversely thereto as did other exposed members of the adjoiner species; (b) separating at least one member of the selected test species into a plurality of components; (c) exposing at least some of the separated components of the member(s) of the test species separately to members of the target species; and (d) examining such exposures to determine for such identification whether members of the target species have been deleteriously affected by such exposures. The test species may be a symbiont or a traditional food source of the adjoiner species. A product including such a test-species component identified as deleteriously affecting members of a target species and/or an equivalent of the identified component is manufactured either by separating the identified component in bulk quantities from members of the test species or by synthesizing the identified component and/or an equivalent of the identified component in bulk quantities. The product is tested to determine the extent of any deleterious effect upon the adjoiner species and the extent of the deleterious effect of the product upon the target species. The method of manufacturing the product may further include modifying the product to decrease any deleterious effect upon the adjoiner species and/or modifying the product to increase the deleterious effect upon the target species.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-29 are cancelled.

\* \* \* \* \*